United States Patent [19]
Elghazzawi

[11] Patent Number: 5,971,930
[45] Date of Patent: Oct. 26, 1999

[54] METHOD AND APPARATUS FOR REMOVING ARTIFACT FROM PHYSIOLOGICAL SIGNALS

[75] Inventor: Ziad Elghazzawi, Medford, Mass.

[73] Assignee: Siemens Medical Systems, Inc., Iselin, N.J.

[21] Appl. No.: 08/951,879

[22] Filed: Oct. 17, 1997

[51] Int. Cl.[6] .................................................. A61B 5/02
[52] U.S. Cl. .................. 600/483; 600/310; 600/479; 600/500; 600/513
[58] Field of Search .................. 600/322–324, 600/364, 481, 483, 454, 479, 500, 513, 519, 521

[56] References Cited

U.S. PATENT DOCUMENTS

| | | | |
|---|---|---|---|
| 4,928,692 | 5/1990 | Goodman et al. | 600/324 |
| 4,955,379 | 9/1990 | Hall | 128/633 |
| 5,111,817 | 5/1992 | Clark et al. | 128/633 |
| 5,113,861 | 5/1992 | Rother | 128/633 |
| 5,351,685 | 10/1994 | Potratz | 128/633 |
| 5,385,144 | 1/1995 | Yamanishi et al. | 128/633 |
| 5,482,036 | 1/1996 | Diab et al. | 600/364 |
| 5,645,060 | 7/1997 | Yorkey | 128/633 |
| 5,749,831 | 5/1998 | Baker | 600/483 |

FOREIGN PATENT DOCUMENTS 0 335 357   10/1989   European Pat. Off. .

*Primary Examiner*—Cary O'Connor
*Assistant Examiner*—Ryan Carter
*Attorney, Agent, or Firm*—Lawrence C. Edelman

[57] ABSTRACT

A heart rate value determined from a first physiological signal that is acquired independently from a second physiological signal, is used to control a band pass filter for controllably bandpass filtering the second physiological signal. In a system having sensors for independently acquiring both electrocardiogram (ECG) and pulse oximetry (SpO2) signals, a heart rate value determined from the ECG signal is used to controllably bandpass filter the red and infrared SpO2 signals, thereby reducing the level of artifact signal in the SpO2 signals.

29 Claims, 1 Drawing Sheet

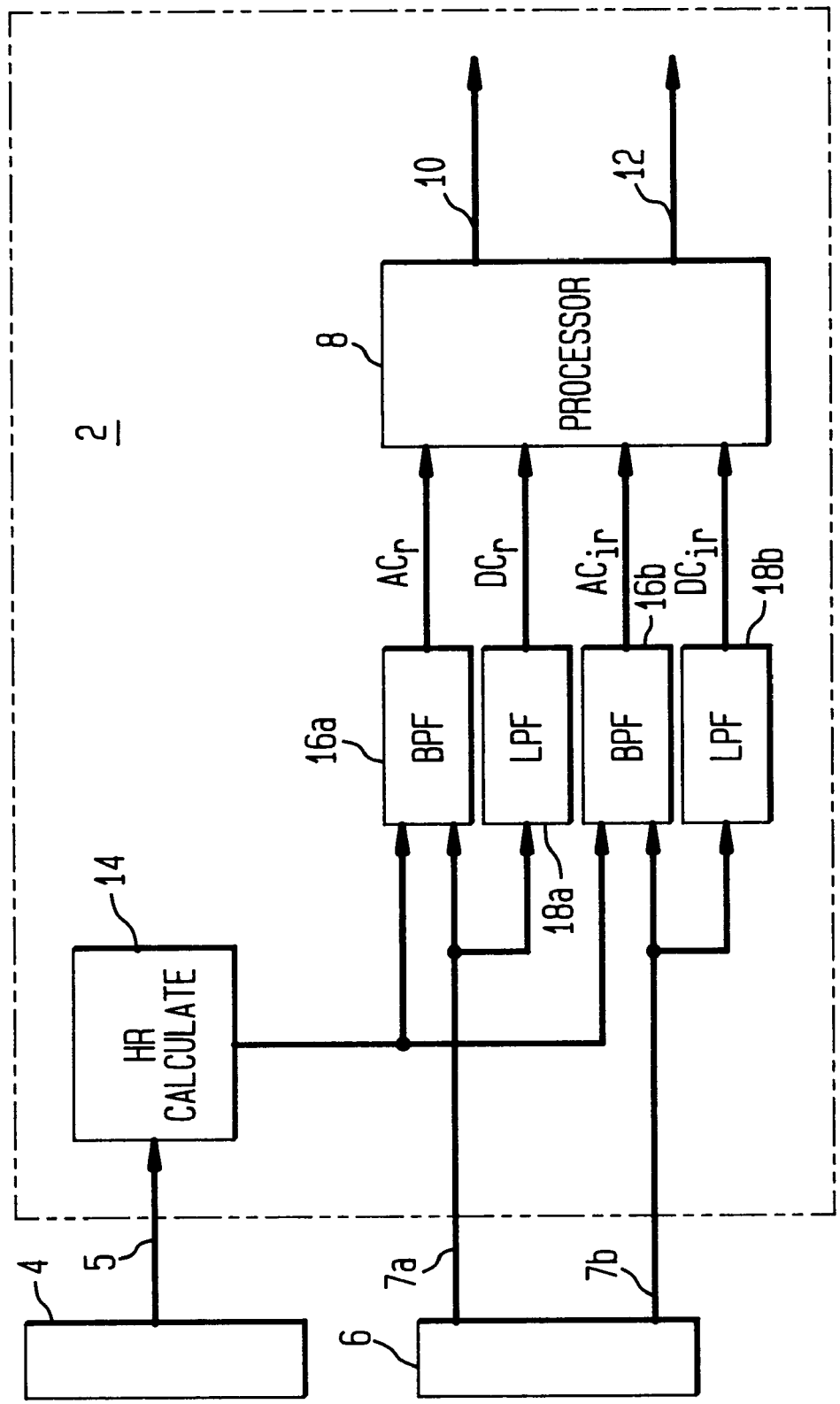

METHOD AND APPARATUS FOR REMOVING ARTIFACT FROM PHYSIOLOGICAL SIGNALS

BACKGROUND OF THE INVENTION

1. Field of the Invention

The present invention relates to a method and apparatus for removing artifact from physiological signals, and more specifically, to using a heart rate value that is determined from a first physiological signal that is acquired independently from a second physiological signal, for controllably bandpass filtering the second physiological signal.

In a system having sensors for acquiring both electrocardiogram (ECG) and pulse oximetry (SpO2) signals, the ECG signal is used to controllably bandpass filter the red and infrared signals acquired by the pulse oximeter. As a result of the invention, more accurate measurement of blood oxygenation and pulse rate is achieved by the oximeter, and the number of false alarms due to erroneous measurements is greatly reduced.

2. Description of the Prior Art

As well known by those of ordinary skill in the art, a pulse oximeter measures arterial blood oxygen saturation and pulse rate using a sensor containing two LED's and a photodiode detector, which is applied directly to a well perfused part of a patient, such as at a finger or ear. The LED's of the sensor apply radiation of two different wavelenghts, commonly red and infrared, to the patient, and the photodiode detector responsive to red and infrared light develops red and infrared electrical signals that are affected, via transmission or reflection, by the patient's blood flow in the area between the two LED's and photodiode detector. The greater the oxygenation of the blood, the less of the emitted red light is detected, due to greater absorption of the red light by the patient's blood. Consequently, the acquired red and infrared signals can be processed to develop a measurement indicative of the blood oxygenation. Additionally, by processing of the pulsatile component of the acquired light signals, a measurment of the pulse rate of the patient can also be developed. As well known, such processing for determining blood oxygenation is based on the ratio of the AC and DC components of the red light compared to the infrared light, such as:

$$\frac{AC_r/DC_r}{AC_{ir}/DC_{ir}}$$

The resultant value is applied to an experimentally-determined reference table to provide the final determination of the acquired measurement of the blood oxygenation.

As well known, the blood oxygenation and pulse rate measurements made from optically acquired signals are highly prone to inaccuracies due to artifacts. Such artifacts typically result from electrical interference (lights, electrosurgical and other electrical equipment near the patient), patient movement (causing a relative movement between the LED's and detector of the sensor, or even worse, the sudden admission of room light into area of the photodiode detector), as well as the fact that the AC component of the acquired signals (which results from the pulsatile characteristic of the blood), is very small, typically on the order of only 1%–5% of the DC value of the acquired signals. Consequently, such artifacts are extremely detrimental to accurate pulse oximetry measurements, and furthermore, can easily lead to the disturbing problem of false alarms.

U.S. Pat. No. 4,955,379 entitled MOTION ARTEFACT REJECTION SYSTEM FOR PULSE OXIMETERS, issued Sep. 11, 1990, discloses the a band-pass filtering (BPF) technique for removing noise artifacts from pulse oximetry signals. More specifically, the AC components of each of the acquired red and infrared signals is initially filtered by a BPF that is broadly tuned to the expected heart rate frequency. The output of the BPF is applied to a frequency determining circuit, whose output is then used to cause the BPF to track the frequency determined by the frequency determining circuit. The theory of this technique is that most of the energy (and information) in the AC signal is contained in at the fundamental frequency, and since the fundamental frequency should be the pulse rate, the frequency determining circuit will determine the pulse rate as the fundamental frequency and control the BPF to exclude all other frequencies, along with artifacts. Unfortunately, it is quite possible that the fundamental frequency determined by the frequency determining circuit may in fact be an artifact signal, such as one that is generated by electrical equipment, causing the oximeter to process the artifact signal and report erroneous information. Consequently, this technique is undesirable.

U.S. Pat. No. 4,928,692 entitled METHOD AND APPARATUS FOR DETECTING OPTICAL PULSES, issued May, 29, 1990, discloses a technique wherein the R-wave portion of a patient's ECG waveform is correlated in time with the optical signals acquired by a pulse oximeter. The correlation is used to develop an enabling signal for processing of the acquired optical signals by the oximeter. The theory is that since the pulse component of the optical signals contain the information, and the occurrence of the optical pulses can be predicted to follow an ECG R-wave by a certain amount, selective timing of oximeter enablement will prevent artifact from being admitted into the oximeter and erroneously processed. Unfortunately, since artifacts can occur at any time, and in general are not in any way correlated so as to have any relation to occurrence of an ECG R-wave, this technique is undesirable.

SUMMARY OF THE INVENTION

In accordance with the principles of the present invention a heart rate value that is determined from a first physiological signal that is acquired independently from a second physiological signal, is used for controllably bandpass filtering the second physiological signal. In a system having sensors for independently acquiring both electrocardiogram (ECG) and pulse oximetry (SpO2) signals, a heart rate value determined from the ECG signal is used to controllably bandpass filter the red and infrared SpO2 signals.

As a result of the invention, more accurate measurement of blood oxygenation and pulse rate is achieved by the oximeter, and the number of false alarms due to erroneous measurements is greatly reduced.

In a preferred embodiment, the heart rate value derived from the ECG signal is used to determine the main frequency of the heartbeat. After determining the main frequency of the heartbeat, a bandpass filter (BPF) having a center frequency centered at the main heartbeat frequency, has one or more of its filter characteristics controlled by value of the determined heartbeat frequency, for filtering the red and infrared SpO2 signals. This method dramatically improves the determination of the AC values of the red and infrared signals. In accordance with a further aspect of the invention the DC part of the red and infrared SpO2 signals are determined as the mean of these signals over a fixed time interval, or by low pass filtering. Once the AC and DC components of the red and infrared signals are determined, the ratio (ACred/DCred)/(ACir/DCir) is used to determine the blood saturation, as well known. By improving the determination of the AC and DC components, the ratio accuracy is improved, and therefore the blood saturation measurement accuracy is improved, specifically for the case where there are small amplitude SpO2 signals and high levels of artifact.

BRIEF DESCRIPTION OF THE DRAWING

The sole FIGURE illustrates in block diagram form the operation of a pulse oximeter in accordance with the principles of the invention.

DETAILED DESCRIPTION OF THE PREFERRED EMBODIMENT

Referring to the FIGURE, a physiological monitor 2 is shown having a first sensor arrangement 4 for acquiring electrocardiogram (ECG) signals 5, and a second sensor arrangement 6 for acquiring red and infrared pulse oximetry (SpO2) electrical signals 7a and 7b. Sensor arrangement 4 may comprise one or more ECG electrodes attached to the chest of a patient, as well known to those in the art, and sensor arrangement 6 may comprise two LED's and a photodiode detector, attached to a well perfused part of the patient, such as a finger or ear, as also well known to those in the art. As previously described, the acquired red and infrared SpO2 signals can be processed to develop measurements indicative of the blood oxygenation and pulse rate of the patient. As well known, such processing for determining blood oxygenation is based on the ratio of the AC and DC components of the red signal compared to the infrared signal, such as:

$$\frac{AC_r / DC_r}{AC_{ir} / DC_{ir}}$$

The resultant value is applied to an experimentally-determined reference table to provide the final determination of the acquired measurement of the blood oxygenation.

Pulse rate can be determined by applying the AC component to a zero-crossing detector and accumulating the count during intervals of one minute or less. A processor 8 is illustrated as being responsive to the AC and DC components of the acquired red and infrared SpO2 signals. Processor 8, using the above noted equation, then develops measurements indicative of the blood oxygenation and pulse rate of the patient, and provides them at outputs 10 and 12, respectively, for application to a display or other interface, not specifically shown, as indications to a user of monitor 2.

As previously noted, the AC components of the acquired SpO2 signals are easily contaminated with artifact signals which disturb their processing, and can easily result in determination of inaccurate measured values and even the generation of false alarms by monitor 2.

As also previously noted, since most of the desired information in the acquired SpO2 signals is located at the fundamental frequency of the component representative of the pulsing blood in the patient, bandpass filtering of the acquired SpO2 signals to select only the fundamental frequency of the pulsatile component for further processing should greatly reduce the level of artifacts that contaminate the acquired SpO2 signals. However, in the forenoted U.S. Pat. No. 4,955,379 the fundamental frequency of the pulsatile component is determined by processing of the acquired SpO2 signals. As previously noted, this technique is undesirable.

Thus, in accordance with a first aspect of the present invention, a heart rate value is obtained independently from the acquired SpO2 signals, namely, from the ECG signal 5 acquired by the separate sensor arrangement 4, and that value is used to controllably bandpass filter each of the acquired SpO2 signals.

More specifically, a heart rate calculator 14 of any of several designs well known to those skilled in the art, calculates the frequency of the heartbeat in units of Hertz. The calculation is done as follows:

$$HMF = \frac{HR}{60}$$

where HMF is the main frequency of the heartbeat in Hertz, and HR is the heart rate in beats per minute.

Next, the filter characteristics of bandpass filters (BPF's) 16a and 16b are controlled by the calculated HMF value, for controllably filtering the red and infrared SpO2 electrical signals 7a and 7b, respectively, before they are applied to processor 8. The same bandpass filter characteristics are used for both of the red and infrared signals. In response to the HMF value, at least one of the passband filter shape, center frequency or bandwidth of each of BPF filters 16a and 16b is controlled in an adaptive manner in response to changes in the frequency of the heartbeat signal as determined by heart rate calculator 14. In a preferred embodiment, filters 16a and 16b may each comprise digital filters, having their coefficients controlled by the output of a look-up table (not specifically shown). The filter coefficients that are output by the look-up table are determined by application of the HMF value thereto as an address, and illustratively cause each filter to have a bandwidth of ±0.5 Hz centered at the changing value of the determined frequency of the heartbeat signal. The thus filtered red and infrared signals are then applied to processor 8. The narrowness of filters 16a and 16b substantially reduce the amplitude of artifact signals in the red and infrared signals, yet, because the passband is centered at the fundamental frequency of the heartbeat signal, the information content of the red and infrared signals is only insignificantly affected.

In accordance with a further aspect of the present invention, in parallel with the forenoted bandpass filtering, the DC components of the red and infrared SpO2 electrical signals are determined using low pass filters (LPF) 18a and 18b having a cut-off frequency of less than 0.5 Hz. Alternatively, the DC components can be determined by calculating the mean value of these signals over a fixed interval of time, such as over a 10 seconds.

Finally, processor 8 determines the pulse rate from the AC components of the red and infrared SpO2 electrical signals, and determines a measurement of the blood oxygenation by the ratio of AC and DC components of the red and infrared signals applied thereto.

Thus, what has been shown and described is a novel method and apparatus for reducing artifact signals in a physiological signal in a manner which fulfills all the advantageous and objects sought therefore. Many changes, modifications, variations and other uses and applications of the subject invention will however be apparent to those of ordinary skill in the art after consideration of this specification and its accompanying drawings, which disclose a preferred embodiment thereof. For example, although in the illustrated embodiment artifact is reduced in an SpO2 physiological signal, the invention can find applicability for reducing artifact in any physiological signal having a pulsatile component. In this regard, although the invention is illustrated in an SpO2 monitor modified to also acquire an ECG signal, the monitor may in fact comprise a multiparameter monitor. Furthermore, it should be understood that the heart rate value can be determined by means other than by use of an ECG signal, and for example, an ultrasound, accelerometer, nuclear magnetic resonance, electrical impedance, or other signal may be used instead. Additionally, although in the illustrated embodiment only the center frequency of PBF's 16a and 16b was controlled, other characteristics of the filters could be adaptively modified, such as bandwidth and/or band shape. In view of the above, the scope of the invention is intended to be limited only by the following claims.

What I claim is:

1. A method for reducing the level of artifact signal in a physiological signal, comprising the following steps:

acquiring a first physiological signal;

acquiring a second physiological signal using an acquisition technique that is different and independant from the technique used to acquire the first physiological signal;

processing the second physiological signal so as to determine a heart rate value therefrom; and using said determined heart rate value for controllably bandpass filtering the first physiological signal and developing an AC component thereof having a reduced level of artifact signal therein.

2. The method of claim 1, wherein:

said first-noted acquiring step acquires red and infrared pulse oximetry signals; and said second-noted acquiring step acquires electrocardiogram signals.

3. The method of claim 2, wherein the processing of the second physiological signal comprises processing electrocardiogram signals for determining a heart rate frequency value.

4. The method of claim 2, including a processing step comprising processing of the red and infrared pulse oximetry signals after being band pass filtered, to develop a measurement of blood oxygenation.

5. The method of claim 4, wherein said processing step processed the red and infrared pulse oximetry signals after being band pass filtered, to develop a measurement of pulse rate.

6. The method of claim 4, wherein the processing step includes processing AC and DC components of the red and infrared pulse oximetry signals in accordance with the following equation:

$$\frac{AC_r/DC_r}{AC_{ir}/DC_{ir}}$$

for developing said measurement of blood oxygenation.

7. The method of claim 4, including a filtering step comprising low pass filtering said red and infrared pulse oximetry signals in parallel with their band pass filtering, to develop DC components thereof.

8. The method of claim 7, wherein said processing step includes processing the AC and DC components of the red and infrared pulse oximetry signals in accordance with the following equation:

$$\frac{AC_r/DC_r}{AC_{ir}/DC_{ir}}$$

for developing said measurement of blood oxygenation.

9. The method of claim 8, wherein said processing step processes the red and infrared pulse oximetry signals after being band pass filtered, to develop a measurement of pulse rate.

10. The method of claim 8, wherein said processing step develops said DC components by determining the mean value of the red and infrared signals over a fixed interval of time.

11. Apparatus for reducing the level of artifact signal in an acquired physiological signal, comprising:

a first sensor arrangement for acquiring a first physiological signal;

a second sensor arrangement for acquiring a second physiological signal using an acquisition technique that is different and independent from the acquisition technique used to acquire the first physiological signal;

a processor responsive to the second physiological signal for determining a heart rate value therefrom; and a bandpass filter responsive to said determined heart rate value for controllably bandpass filtering the first physiological signal and developing an AC component thereof having a reduced level of artifact signal therein.

12. The apparatus of claim 11, wherein:

said first sensor arrangement acquires red and infrared pulse oximetry signals; and said second sensor arrangement acquires electrocardiogram signals.

13. The apparatus of claim 12, wherein said processor processes said electrocardiogram signal so as to determine a heart rate frequency value from said electrocardiogram signals.

14. The apparatus of claim 12, wherein said processor is responsive to the red and infrared pulse oximetry signals after they are band pass filtered, for developing a measurement of blood oxygenation.

15. The apparatus of claim 14, wherein said processor is responsive to the red and infrared pulse oximetry signals after they are band pass filtered, for developing a measurement of pulse rate.

16. The apparatus of claim 14, wherein said processor processes AC and DC components of the red and infrared pulse oximetry signals in accordance with the following equation:

$$\frac{AC_r/DC_r}{AC_{ir}/DC_{ir}}$$

for developing said measurement of blood oxygenation.

17. The apparatus of claim 14, further including a low pass filter for filtering said red and infrared pulse oximetry signals in parallel with their band pass filtering, to develop DC components thereof.

18. The apparatus of claim 17, wherein said processor processes AC and DC components of the red and infrared pulse oximetry signals in accordance with the following equation $$\frac{AC_r/DC_r}{AC_{ir}/DC_{ir}}$$

for developing said measurement of blood oxygenation.

19. The apparatus of claim 18, wherein said processor is responsive to the red and infrared pulse oximetry signals after they are band pass filtered, for developing a measurement of pulse rate.

20. The apparatus of claim 18, wherein said processor develops said DC components by determining the mean value of the red and infrared signals over a fixed interval of time.

21. An oximeter for determining a blood oxygenation level of a patient, comprising:
   an oximeter sensor arrangement coupled to the patient for acquiring a blood oxygenation signal having an undesirable artifact signal component;
   an additional sensor arrangement coupled to the patient for acquiring an additional signal representative of a physiological condition of the patient using an acquisition technique that is independent of the acquisition technique used to acquire the blood oxygenation signal;
   a processor responsive to the additional signal for determining a value therefrom representative of the heart rate of the patient; and
   a filter responsive to said determined heart rate value for controllably filtering the blood oxygenation signal in response to changes in the value of the patient's heart rate, for developing an AC component for the blood oxygenation signal which has a reduced level of said artifact signal therein.

22. The oximeter of claim 21, wherein said additional sensor arrangement acquires an electrocardiogram signal.

23. The oximeter of claim 21, wherein said filter comprises a bandpass filter having at least one of its filter characteristics controlled by said heart rate value.

24. The oximeter of claim 23, wherein said bandpass filter has its center frequency controlled by said heart rate value.

25. The oximeter of claim 23, wherein said processor is responsive to the blood oxygenation signal after it has been bandpass filtered, for developing a measurement of blood oxygenation of said patient.

26. The oximeter of claim 23, wherein said processor is responsive to the blood oxygenation signal after it has been bandpass filtered, for developing a measurement of pulse rate of said patient.

27. The oximeter of claim 25, wherein:
   said first sensor arrangement acquires red and infrared pulse oximetry signals; and,
   said processor processes AC and DC components of the red and infrared pulse oximetry signals in accordance with the following equation:

$$\frac{AC_r/DC_r}{AC_{ir}/DC_{ir}}$$

for developing said measurement of blood oxygenation.

28. The oximeter of claim 27, further including a low pass filter for filtering said red and infrared pulse oximetry signals in parallel with their bandpass filtering, to develop DC components thereof.

29. The oximeter of claim 25, wherein said processor is responsive to the red and infrared signals over a fixed interval of time for determining the mean value of said signals as said DC components.

* * * * *